United States Patent [19]

Hartlaub et al.

[11] 4,337,777
[45] Jul. 6, 1982

[54] RATE LIMITED PACER

[75] Inventors: Jerome T. Hartlaub, New Brighton; Ray S. McDonald, St. Paul; Lawrence C. Hudziak, White Bear Lake, all of Minn.

[73] Assignee: Medtronic, Inc., Minneapolis, Minn.

[21] Appl. No.: 220,204

[22] Filed: Dec. 24, 1980

[51] Int. Cl.³ .............................................. A61N 1/36
[52] U.S. Cl. ........................................... 128/419 PG
[58] Field of Search ................................ 128/419 PG

[56] References Cited

U.S. PATENT DOCUMENTS

| | | |
|---|---|---|
| 3,903,897 | 9/1975 | Woolons et al. ............. 128/419 PG |
| 3,920,024 | 11/1975 | Bowers ......................... 128/419 PG |
| 4,038,991 | 8/1977 | Walters ......................... 128/419 PG |

*Primary Examiner*—William E. Kamm
*Attorney, Agent, or Firm*—Robert C. Beck; John L. Rooney; Joseph F. Breimayer

[57] ABSTRACT

A pacer having an upper and lower rate limit system for preventing pacer malfunction from producing pacer output pulses above or below preset maximum and minimum rates.

4 Claims, 5 Drawing Figures

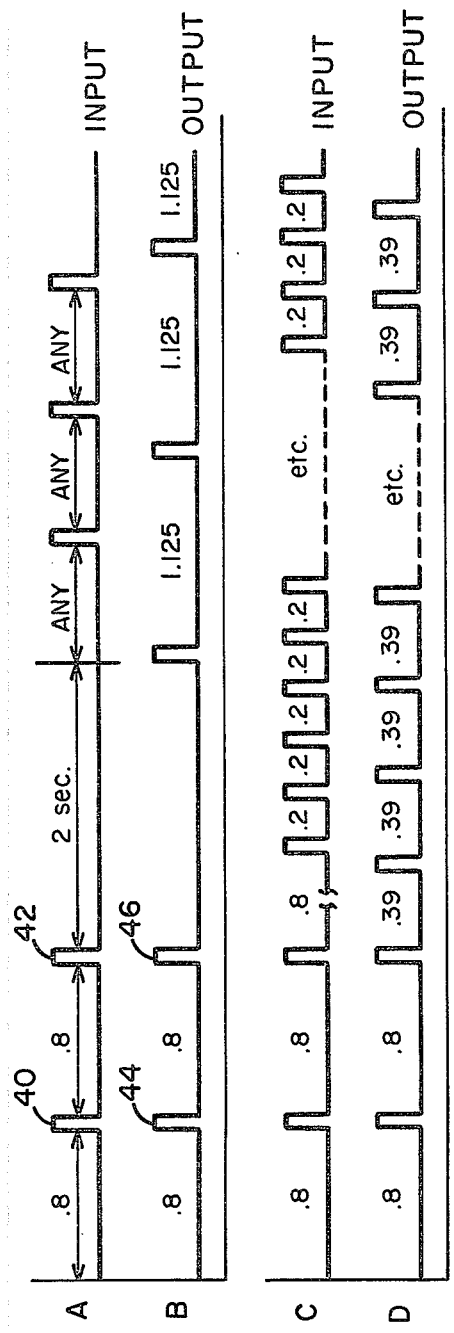
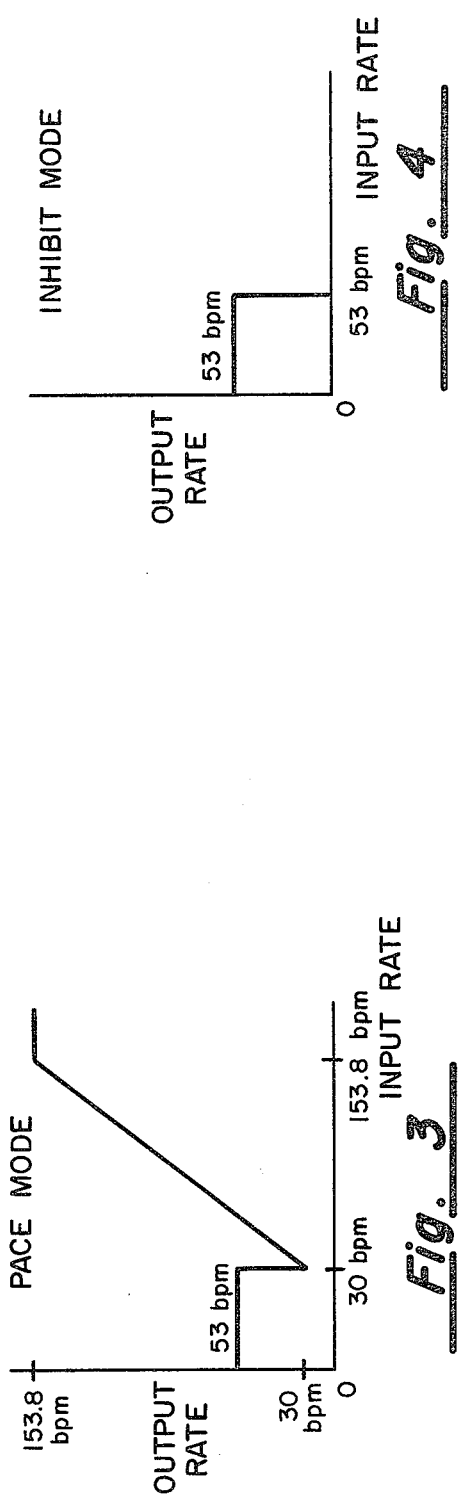

RATE LIMITED PACER

BACKGROUND OF THE INVENTION

1. Field of the Invention

This invention relates to pacers for the therapeutic stimulation of the heart.

2. Description of the Prior Art

Pacers for stimulating the heart are well known in the art. Traditionally these devices have been manufactured utilizing discrete analog circuitry of limited complexity. More recently, however, pacers have been designed and manufactured with integrated digital circuitry of great complexity. This additional capability has been used to add desirable features such as telemetry and programmability to these modern pacers.

The programmability feature permits the attending physician to noninvasively alter a pacer parameter such as pacer rate. Typically, the value of the selected parameter is stored locally within the pacer in a volatile semiconductor memory. One problem associated with pacers operating under the control of locally stored data relates to failure modes resulting from the loss of this stored information. These software driven pacers are susceptible to unintentional memory change or phantom programming caused by electromagnetic interference. This interference may result in an alteration in memory contents and result in pacing at a rate substantially different from that previously programmed into the pacemaker by the attending physician. As a consequence, these software related errors may result in pacer-induced bradycardia or pacer-induced tachycardia which forces the heart to operate outside physiologically safe limits.

One prior art solution directed to the problem of pacer induced tachycardia is taught by U.S. Pat. No. 3,391,697 to W. Greatbatch. One embodiment taught by this patent involves the use of circuitry interposed between the oscillator rate determining portion of the pacemaker and the output portion of the pacemaker. In operation the rate limit system prevents stimulating pulses from being delivered to the heart above a preset upper frequency limit. This form of rate runaway protection has been widely adopted and prevents single component failures in the pacer from producing a life-endangering rate runaway condition.

Although this technique has been widely adopted in modern digital pacemakers, it does not address the low rate failure mode nor the other problems faced by pacers operating under the control of stored data.

A further prior art patent which relates generally to rate limit techniques for pacers is the U.S. Pat. No. 3,903,897 to Woolons, et al., which describes generally an A-V sequential pacer with upper and lower rate limit circuits. In this pacer, synchronizing pulses derived from the atrial or ventricular cardiac depolarization are ignored beyond the preset upper and lower rate limits. If these rate limits are exceeded, asynchronous pacing pulses are produced in a reversion mode. This rate limit technique does not address nor is it applicable to the problems posed by pacers operating under the control of stored data but is concerned only with the effect on the pacer of several depolarizations exceeding the upper rate limit or falling below the lower rate limit.

Pacers operating under the control of stored data are known in the art from commonly assigned, copending U.S. patent application Ser. No. 957,959 filed Nov. 6, 1978 now U.S. Pat. No. 4,253,465. Programmable pacers of this type have a number of critical operating parameters stored in a volatile semiconductor memory. The loss of this information through phantom programming or through other means may result in output pulses being delivered at a rate outside of physiologically safe limits.

SUMMARY OF THE INVENTION

In contrast, the rate limited pacer of the present invention includes circuitry for insuring that the loss of information stored in a local memory will still result in stimulating pulses delivered to the heart which are between a physiologically safe upper and lower limit.

This function is achieved by inserting novel rate limit logic between the pulse-forming portion of the pacer and the output or pulse delivery portion of the pacer. In this configuration, the rate limit logic accepts a pacer rate input signal from the pulse-forming circuitry and produces an output pulse rate signal which is confined between preset limits. The structure of the rate limit logic which achieves this function includes a monitor for detecting state transitions of the input signal and timer apparatus for insuring that the input signal meets preset timing criteria.

In the event that the input signal exceeds a physiologically safe upper rate limit, the timing circuitry prevents stimulating pulses from reaching the heart sooner than a preset maximum rate interval.

In the event that the pacer logic produces an input rate signal below a physiologically safe limit as defined by a dropout rate interval, the rate limit logic will act to produce stimulating pulses at a preset minimum rate.

BRIEF DESCRIPTION OF THE DRAWINGS

FIG. 2 is a timing diagram showing the operation of the rate limit logic of the invention, FIG. 3 is a graphic representation of the output pulse rate as a function of input pulse rate for the inhibited mode;

FIG. 4 is a graphic representation for the pace mode; and

DESCRIPTION OF THE PREFERRED EMBODIMENT

Figure 1:
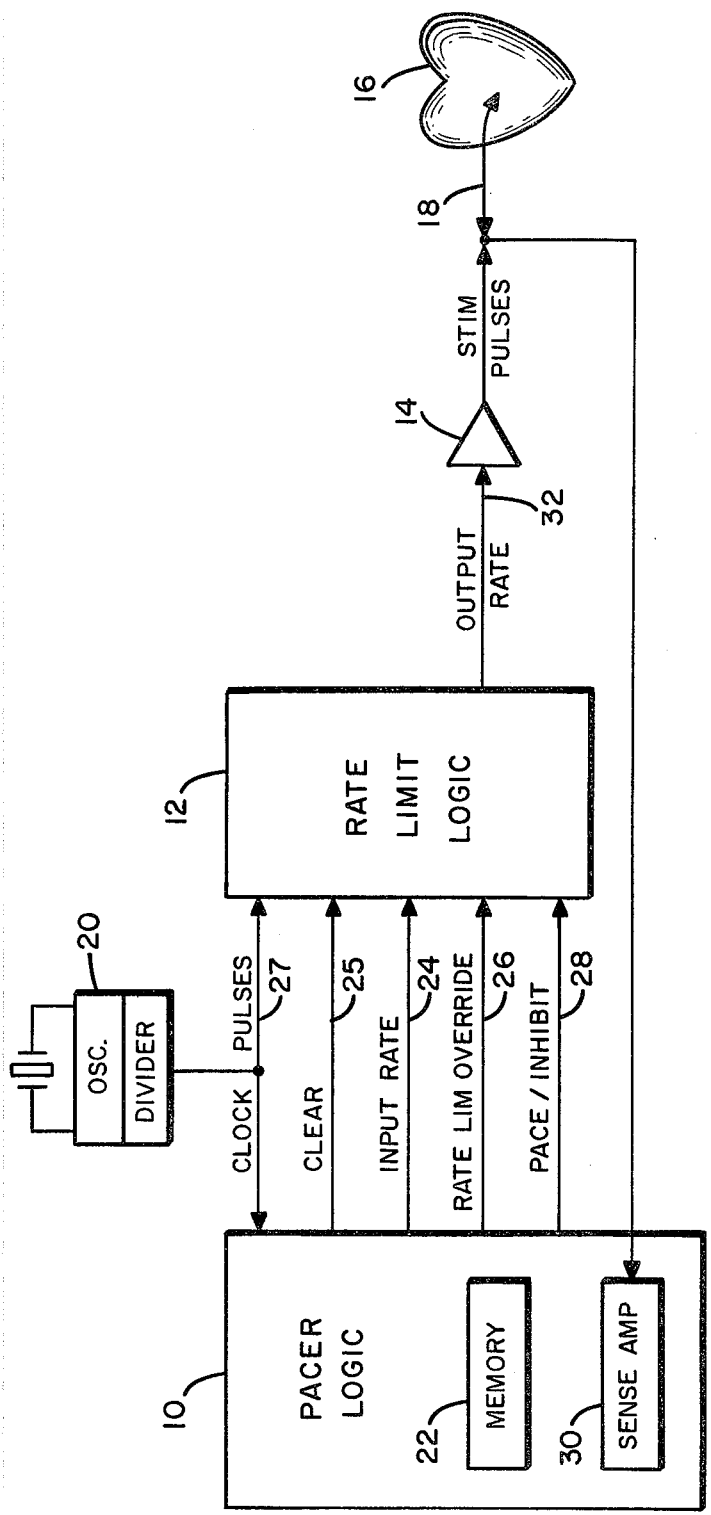
FIG. 1 is a block diagram showing the functional organization of the rate limited pacer.

The rate limited pacer shown in FIG. 1 comprises pacer logic 10 for producing pulses at a rate depending upon the contents of memory 22 and sensed cardiac activity communicated to sense amplifier 30 from the heart. This pulse-forming portion of the pacer delivers pulses to the rate limit logic 12. The rate limit logic monitors the input rate through a rate input connection 24 and produces a corresponding output rate if the input rate is between preset upper and lower rate limits. The output rate is delivered to the output amplifier 14 through a connection 32.

The rate limit logic 12 is controlled from the pacer logic 10 by means of three control signals labeled CLEAR 25, RATE LIMIT OVERRIDE 26, and PACE/INHIBIT 28 and a CLOCK signal 27 as shown in FIG. 1. Each of these control signals developed by the pacer logic modifies the operation of the rate limit logic 12.

For example, the CLOCK signal 27 derived from the 32.768 KHz crystal oscillator provides the basic 1.024 KHz timing information for the various rate limits. The PACE/INHIBIT signal 28 is a one-bit control which forms the rate limit logic whether the pacemaker is operating in an inhibited mode or is supplying pacing pulses to the heart. A logic 0 on the PACE/INHIBIT control line 28 corresponds to operation of the pacemaker in the inhibited mode and prevents input rate signals from generating a corresponding output rate signal.

The RATE LIMIT OVERRIDE control signal 26 is at the logic 1 voltage level during normal operation of the implanted pacemaker which permits the rate limit logic to operate in a protective fashion. However, for some diagnostic purposes it is desirable to permit the output stimulus rate to range beyond the normally physiologically safe rates. A logic 0 at the RATE LIMIT OVERRIDE control signal 26 will disable the rate limiting logic and permit the output rate to track the corresponding input rate beyond the preset maximum and minimum rates.

The CLEAR control signal 25 is a one-bit control which is at the logic 0 voltage level during normal operation of the pacemaker. If the pacer logic 10 results in a rate applied to the input rate line 24 which is below the physiologically safe limits, the rate limit logic will latch into a minimum rate mode and produce output pulses at a minimum stimulus rate until this mode is reset by the application of a logic 1 voltage level to the clear input 25.

In summary, the rate limited pacer shown in FIG. 1 includes rate limit logic which receives an input rate signal from rate determining pacer logic 10 as well as a number of clock and control signals and produces an output rate which is between physiologically safe limits for the heart thus preventing component failure or misprogramming of the pacer logic 10 from resulting in pacer-induced tachycardia or bradycardia.

Turning to FIG. 2 the operation of the rate limit logic 12 in response to low input rates and high input rates is shown graphically.

Waveform A represents the input rate available on lead 24 produced by the pacer logic 10 and delivered to the rate limit logic 12. The corresponding lower waveform B presents the output rate 32 of the rate limit logic in response to the input waveform. In the figure, pulses 40 and 42 represent ventricular stimulating pulses separated by 0.8 second intervals which correspond to approximately 72 bpm pacing rate. The rate limit logic responds by delivering corresponding ventricular stimulating pulses 44 and 46 to the output amplifier buffer 14 for delivery to the heart. If no input rate pulses are detected for a two-second dropout interval, then the low rate logic will supply ventricular stimulating output pulses on line 32 at a preset minimum rate shown in the figure as 1.125 seconds corresponding to a 53.3 bpm pacing rate for a 1.024 KHz clock signal.

If the input rate to the rate limit logic 12 exceeds an upper rate as shown in FIG. 2 waveform C, then the output rate 32 from the rate limit logic 12 will be at an upper rate limit corresponding to the 0.390 second interval shown on waveform D which corresponds to the pacing rate of 153.3 bpm. This mode of operation described with respect to FIG. 2 is shown diagrammatically on FIG. 3 which shows the output rate as a function of the input rate for the pace mode. When the pacemaker is inhibited, however, no output stimulating pulses would be delivered to the amplifier buffer 14 by the rate limit logic. This is shown in FIG. 4. However, in both modes the rate limit logic 12 will continue to monitor the input rate which may be generated for use elsewhere within the pacemaker logic 10. Thus, in the inhibit mode as shown in FIG. 4, the output of rate limit logic 12 will be 53.3 bpm only if the input rate to the rate limit logic is below 53.3 bpm.

Figure 5:
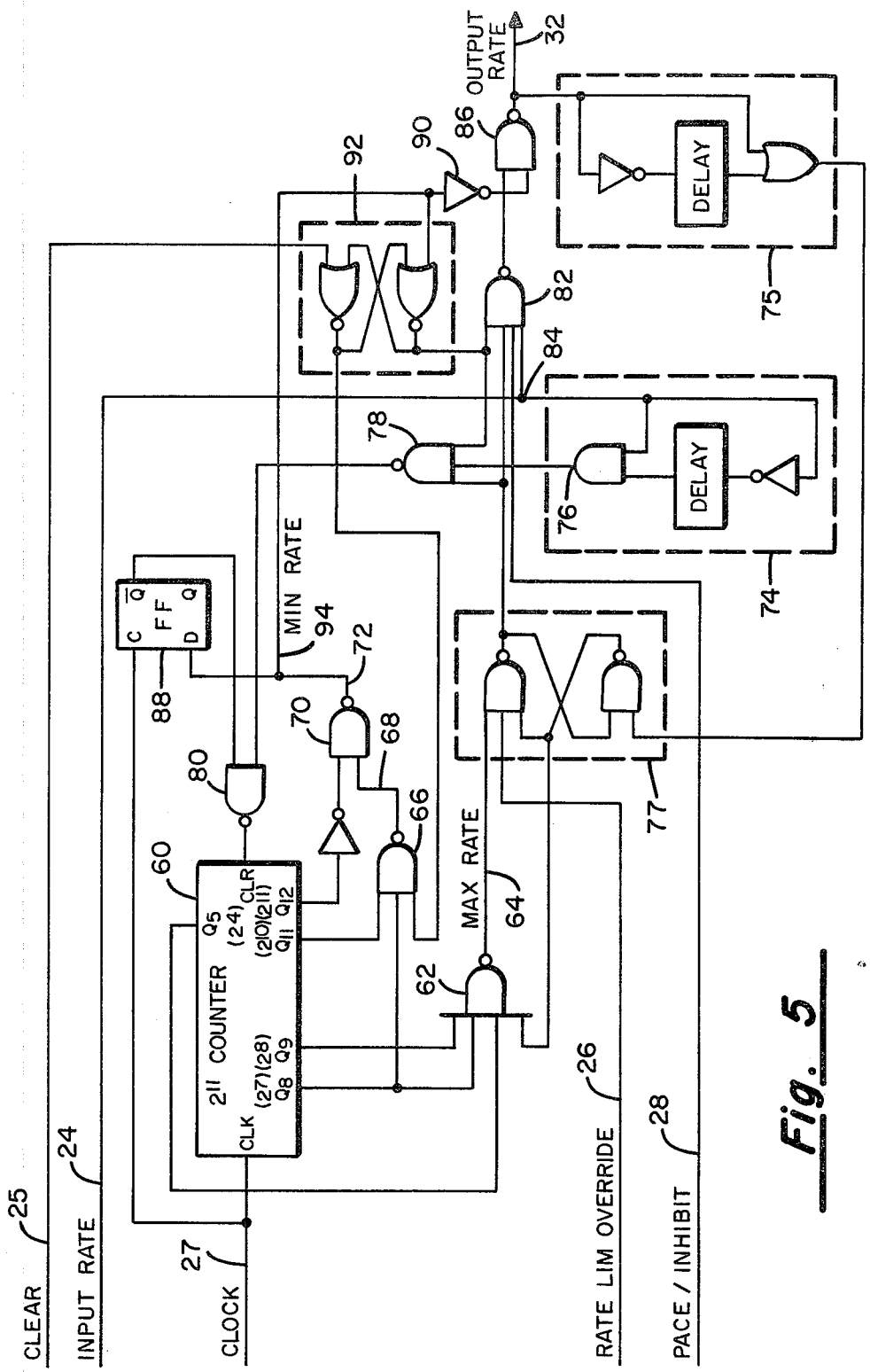
FIG. 5 is a logic schematic of one implementation of the rate limit logic of the rate limit pacer.

Turning to the logic schematic of FIG. 5, one method for implementing the novel rate limit logic of the present invention is shown. The input rate at input rate connection 24 is passed through logic to the output rate terminal 32 if the input rate waveform meets certain preset repetition rate criteria. If the input rate drops below a minimum preset level, then the logic shown in FIG. 5 will produce output signals at a preset minimum rate. If, on the other hand, the input rate exceeds a predetermined maximum, then the logic shown within FIG. 5 will act to prevent stimulating pulses from reaching the output rate terminal 32 beyond a preset rate.

More specifically, the 12-stage ripple counter 60 receives 1.024 KHz clock pulses from a clock input line 27. The Q outputs of ripple counter 60 go high in sequence, and combinatorial logic operating on the Q outputs may be used to produce logic states at preset time intervals. For example, as shown in the diagram, the Q5, Q8 and Q9 outputs, which correspond to $2^4$, $2^8$ and $2^8$ counter states, respectively, of counter 60 are supplied to NAND gate 62 which will produce a logic 1 output level on lead 64 on a periodic basis. The 12-stage ripple counter shown in the diagram when clocked with a 1.024 KHz clock signal will produce a logic 1 on output line 64 once every 0.39 seconds. Likewise, the Q8, Q11 inputs to NAND gate 66 will produce a logic 1 state on lead 68 once every 1.125 seconds, and the combinatorial inputs to NAND gate 70 will produce an output signal on lead 72 once every 2 seconds. In operation, the counter 60 is reset by each detected logic transition on the input line 24, and some of the combinatorial outputs just described are not produced during normal pacer operation.

In operation, an edge-triggered logic unit 74 monitors the input rate 24 and produces a brief output pulse available at node 76 during each positive-going transition of the input rate signal. This signal, in combination with others, activates NAND gate 78 which reset counter 60 through NAND gate 80 at the trailing edge of each input rate signal. As a consequence, counter 60 counts from 0 at the positive edge of each input rate signal. The MAX rate limit line 64 changes state at the end of a 390 millisecond timing interval set by counter outputs Q5, Q8 and Q9. This logic state is utilized to enable NAND gate 82 via flip-flop 77 which permits input rate signals coupled to NAND 82 to toggle the output of NAND gate 86, thus producing an output on output lead 32. Consequently, the timing interval established by counter 60 permits the output rate to track with the input rate as long as the frequency of the input rate does not exceed the maximum rate set by the time interval of counter 60.

The lower rate limit feature operates as follows. If no edge is detected by edge detector 74 within a two-second time interval established by Q12 on counter 60 then flip-flop 88 will latch, placing a logic 0 on NOTQ output of flip-flop 88 thus resetting counter 60. The flip-flop delays the rest of counter 60 by one clock cycle to prevent a race condition with the $2^{11}$ state output of the counter. This also provides the timing for the MIN rate pulse width. The logic transition which latches flip-flip 88 also delivers a MIN rate signal to inverter 90, which toggles output gate 86 and produces a stimulus pulse two seconds after the last detected state transition of the input rate line. This signal latches RS type flip-flop 92 and produces a logic level on NAND gate 66 which permits additional pulses from counter 60 corresponding to the counts of Q8 and Q11 to be coupled via lead 94 to the output rate terminal 32. Also, note that the output pulse from gate 86 triggers the edge detector 75. This circuit triggers on the trailing edge of each output pulse and resets the MAX rate flip-flop 77 to disable the output for a 390 ms time interval.

Thus, after a two-second delay following the last detected logic transition of the input rate, the low rate limit logic will operate as an asynchronous timer producing output stimuli at node 32 at a preset rate corresponding to 1.125 seconds or about 53.3 bpm. To escape from this low rate mode a logic 1 level must be placed on clear line 25 to reset the flip-flop 92. This may be accomplished by the attending physician by reprogramming the pacer, or by pacer logic.

It should be apparent that numerous modifications of the apparatus may be made without departing from the scope of the invention.

We claim:

1. A rate limited pacer comprising:
   an oscillator for providing clock pulses at a clock rate;
   memory means for storing parameter data;
   pacer logic means for producing an input rate signal in response to stored parameter data and said clock pulses; and
   rate limit logic means responsive to said input rate signal and said clock pulses for producing an output rate signal equal to said input rate signal if said input rate signal is between an upper maximum rate limit and a lower dropout rate limit and for producing an output rate substantially equal to said maximum rate limit if said input rate signal exceeds said maximum rate limit and for producing an output rate at a minimum rate if said input rate is lower than said dropout rate.

2. The pacer of claim 1 wherein said rate limit logic means includes:
   monitor means detecting input signal state transitions producing a counter reset signal in response to state transitions;
   counter means responsive to said clock pulses for producing a minimum rate interval signal, a maximum rate interval signal and a dropout rate interval signal;
   first means responsive to said maximum rate interval signal for gating said input signal to said output signal means when said input signal period exceeds said maximum rate interval;
   second means responsive to said dropout interval signal for preventing counter reset signals from resetting said counter; and
   third means responsive to said dropout interval signal for producing an output rate at a frequency corresponding to said minimum rate interval.

3. The pacer of claim 1 wherein said rate limit logic includes:
   monitor means detecting input signal state transitions producing a counter reset signal in response to state transitions;
   counter means responsive to said clock pulses for producing a first minimum rate interval signal, a second maximum rate interval signal and a third dropout rate interval signal;
   first logic means responsive to said maximum rate interval signal for gating said input signal to said output signal means when said input signal period exceeds said maximum rate interval;
   second logic means responsive to said dropout interval signal for preventing counter reset signals from resetting said counter; and
   third logic means responsive to said dropout interval signal for producing an output rate at a frequency corresponding to said minimum rate interval.

4. The pacer of claim 1 wherein said rate limit logic includes:
   monitor means for detecting the state of said input signal;
   counter means responsive to said clock pulses for producing a first minimum rate interval signal, a second maximum rate interval signal and a third dropout rate interval signal;
   first logic means responsive to said maximum rate interval signal for gating said input signal to said output signal means when said input signal period exceeds said maximum rate interval;
   second logic means responsive to said dropout interval signal for preventing counter reset signals from resetting said counter; and
   third logic means responsive to said dropout interval signal for producing an output rate at a frequency corresponding to said minimum rate interval.

* * * * *

UNITED STATES PATENT AND TRADEMARK OFFICE
CERTIFICATE OF CORRECTION

PATENT NO. : 4,337,777
DATED : July 6, 1982
INVENTOR(S) : HARTLAUB et al

It is certified that error appears in the above-identified patent and that said Letters Patent are hereby corrected as shown below:

Column 3,
　　　Line 5, "forms" should be --informs--.

Signed and Sealed this

Second Day of November 1982

[SEAL]

Attest:

GERALD J. MOSSINGHOFF

Attesting Officer　　Commissioner of Patents and Trademarks